(12) United States Patent
Goishihara

(10) Patent No.: US 7,563,534 B2
(45) Date of Patent: Jul. 21, 2009

(54) PACKAGE CONTAINING ROLL OF LONG ELECTRODE PLATE

(75) Inventor: Satoshi Goishihara, Tokyo-to (JP)

(73) Assignee: Dai Nippon Printing Co., Ltd., Tokyo-to (JP)

( * ) Notice: Subject to any disclaimer, the term of this patent is extended or adjusted under 35 U.S.C. 154(b) by 847 days.

(21) Appl. No.: 10/899,973

(22) Filed: Jul. 27, 2004

(65) Prior Publication Data

US 2005/0058889 A1   Mar. 17, 2005

(30) Foreign Application Priority Data

Aug. 1, 2003 (JP) .............. 2003-284958
Sep. 25, 2003 (JP) .............. 2003-332834

(51) Int. Cl.
- H01M 4/00 (2006.01)
- H01M 2/10 (2006.01)
- B65D 81/20 (2006.01)
- F16B 37/04 (2006.01)

(52) U.S. Cl. .............. 429/94; 429/96; 206/524.8; 411/180

(58) Field of Classification Search ............ 429/94, 429/96; 206/524.8; 411/180
See application file for complete search history.

(56) References Cited

U.S. PATENT DOCUMENTS

| | | | | |
|---|---|---|---|---|
| 1,809,267 A | * | 6/1931 | Cushing | 206/415 |
| 4,756,422 A | * | 7/1988 | Kristen | 206/524.8 |
| 5,804,330 A | * | 9/1998 | Miyazaki et al. | 429/48 |
| 2002/0021948 A1 | * | 2/2002 | Stumpf et al. | 411/180 |

FOREIGN PATENT DOCUMENTS

| | | |
|---|---|---|
| JP | 10-45163 A | 2/1998 |
| JP | 10-069899 | 3/1998 |
| JP | 11-278580 | 10/1999 |
| JP | 2001-192004 A | 7/2001 |

* cited by examiner

*Primary Examiner*—Dah-Wei D Yuan
*Assistant Examiner*—Zachary Best
(74) *Attorney, Agent, or Firm*—Ladas & Parry LLP

(57) ABSTRACT

A package containing a roll of a long electrode plate which is a package for storing a roll of a long electrode plate, making it is possible to simplify the work process of containing and packaging the roll of a long electrode plate and prevent the electrode performance from deterioration without the electrode plate to absorb moisture, be damaged or the like, and the collection of packaging material constituting the package is not necessary since the packaging material is disposable after opening of the package.

4 Claims, 4 Drawing Sheets non-formed portion    active material layer non-formed portion    active material layer collector    active material layer non-formed portion terminal active material layer active material layer collector terminal

PACKAGE CONTAINING ROLL OF LONG ELECTRODE PLATE

BACKGROUND OF THE INVENTION

1. Field of the Invention

The present invention relates to a package containing a roll of a long electrode plate for storage.

2. Description of the Related Art

In recent years, reduction in size and weight of electronic equipment and communication equipment has rapidly been advanced. This advance has also required reduction in size and weight of secondary batteries used as driving power sources for these equipments. For these demands, there have been developed nonaqueous electrolyte secondary batteries having high energy density and high voltage, typically, a lithium ion secondary battery, in place of conventional alkaline batteries.

A positive electrode plate and a negative electrode plate have large influence on the performance of the secondary battery, thus it is emphasized to reduce the thickness and enlarge the area of the electrode plates to be wound in the battery in order to elongate the life span of a charge/discharge cycle, and to have high energy density.

In the production of such an electrode plate, for example, as shown in FIG. 1 (herein, FIG. 1A is a plan view, and FIG. 1B is a side view.), an active material layer having a function of emitting lithium ions (i.e., a positive electrode plate) or an active material layer having a function of adsorbing these lithium ions (i.e., a negative electrode plate) is formed on a collector made of an aluminum foil, a copper foil or the like. There is provided a portion wherein the active material layer is not formed (a portion wherein the electrode plate is exposed) as a portion to which a terminal is to be connected in a pattern form.

The electrode plate is cut along a dotted line as shown in FIG. 1A, and divided into a long plate form of a width corresponding to the size of a battery to be finally assembled, as shown in FIG. 2. Herein, a long plate form refers to a thin flat tape-like form. An interval between the plural portions to which the terminals are to be connected on the long electrode plate is decided in accordance with the size of a battery to be finally assembled.

The positive or negative long electrode plate is, for example, a long plate having length of about 200 to 500 m in the direction of conveyance (in longitudinal direction), and is wound in a rolled form to be handled in a discal state which has, for example, an outside diameter of about 20 to 40 cm, and the thus wound long plate is used in an assembling step of the battery.

Both positive and negative long electrode plates are released from a roll, and cut in a certain length. In the assembling step of the battery, the positive long electrode plate and the negative long electrode plate are rolled together disposing a separator therebetween, and contained in a battery case for use. In such a process of producing a long electrode plate through an assembling step of the battery, there is a strict condition that the moisture absorption of the electrode plate should be completely prevented since the moisture absorption of the electrode plate causes deterioration of the electrode performance and increase in thickness of an active material layer so that an electrode plate cannot be contained inside of a battery of a certain size. Also, other problems besides the moisture absorption often occur such as heating generation due to electrical short-circuit, which occurs when an electrode plate receives an external collision or is put straight to store or transfer in a rolled form and damaged near grounding by its own weight. In order to overcome these moisture absorption and damage problems, conventionally, a wide long electrode plate has been produced to cut in a certain width, the long plate is wound in a rolled form and subjected to vacuum drying, and then the wound plate has been stored in a airtight container such as a plastic bag, and it has been transported in this state, until the assembling step of the battery has been carried out. The assembling step has been carried out in a room the atmosphere of which was kept in a dried condition.

Further, it is not limited to the electrode plate for the lithium-ion battery, but also an electrode plate for an electric double layer capacitor, an electrode plate for a fuel cell or the like are handled in a state, as shown in FIG. 3 (herein, FIG. 3A is a plan view, and FIG. 3B is a side view.), that an electrode plate, which has an active material layer formed on one surface of a long (consecutive) collector (an electrode substrate), is continuously wound to a take-up core. The electrode plate is cut along a dotted line, as shown in FIG. 3A, in a plate form of a width corresponding to the size of a battery to be finally assembled, as shown in FIG. 4, and a terminal is connected on an opposite surface of the collector wherein the active material layer is formed to be used accordingly.

In carrying out the above method, when a roll of a long electrode plate is contained or conveyed, for example, as shown in Japanese Patent Application Laid-Open (JP-A) No. 10-69899, the roll of a long electrode plate is fixed to be contained in a sealed container having a tape pulling-out opening formed. The tape pulling-out opening of the sealed container is sealed with a sealing seal. A core of the roll of a long electrode plate and a side plate of the sealed container are fixed with the use of a bolt which is a side plate fastening means by a screw cramp wherein an inside diameter of the core and the bolt intermesh.

However, when using the above sealed container, there is a problem that it takes a lot of trouble with axial rotation of the fastening means of the bolt in a bore of the core.

It is mentioned in JP-A No. 10-69899 that the fastening means of the bolt may be pushed inside of a core without rotating the fastening means of the bolt, however, in the packing form using the sealed container as mentioned above, the sealed container is not discarded when it is used once. Packing members are expensive and based on the premise that after the members are used once, the members are collected for reuse. Thus, there is a problem that if a long electrode plate is transported abroad in a packing form of a roll of a long electrode plate, it is particularly costly to collect the packing members.

Also, an electrode plate contained in a sealed container disclosed in JP-A No. 10-69899 is used by connecting the roll of an electrode plate kept in the sealed container on an electrode take-up device and rotating the roll of an electrode plate.

SUMMARY OF THE INVENTION

An object of the present invention is to provide a package containing a roll of a long electrode plate for storage, wherein it is possible to simplify the work process of containing and packaging the roll of a long electrode plate and prevent the electrode performance from deterioration without the electrode plate to absorb moisture, be damaged or the like, and the collection of packaging material comprising the package is not necessary after opening of the package since the packaging material is disposable.

In order to attain the above object, the present invention is a package containing a roll of a long electrode plate, wherein a cushioning having a hole and a flange having a hole are respectively arranged in this order on both side surfaces of a roll of a long electrode plate comprising a core (or spindle) having a hole and a long electrode plate, which is wound to the core, or on both side surfaces of a group of rolls of a long electrode plate comprising two or more rolls of a long electrode plate and one or more cushionings disposed alternatively so that the side surfaces of the rolls of a long electrode plate are located next to each other disposing the cushioning having a hole therebetween, so as to align the core hole, the cushioning hole and the flange hole; the roll of a long electrode plate, the cushioning and a core cap are assembled by fitting a cylindrical portion of the core cap from the flange hole side, the core cap comprising the cylindrical portion, which fits into each hole, and a collar portion; and further the roll of a long electrode plate is packed to seal with at least dry gas and/or desiccating agent so that the pair of flanges is grounded to suspend and support the roll of a long electrode plate by making both configurations of the pair of flanges larger than that of the roll of a long electrode plate in order to prevent the roll of a long electrode plate from being grounded.

The package containing a roll of a long electrode plate of the present invention takes no trouble with axial rotation of a screw bolt at the time of fixing a core of the roll of a long plate and a flange. The flange and the core are adhered each other and fixed disposing a cushioning therebetween on both side surfaces of the roll of a long electrode plate by fitting a cylindrical portion into each hole of the flange, the cushioning and the core using a core cap comprising the cylindrical portion and a collar portion. Thereby, both right and left side surfaces of the roll of a long electrode plate are protected by the cushioning and the flange. Also, both configurations of a pair of flanges are larger than that of the roll of a long electrode plate, thus the pair of flanges is grounded to suspend and support the roll of a long electrode plate in the state that the roll of a long electrode plate is not grounded. Further, since gas is fed to the roll of a long electrode plate and packed, it is possible to prevent an electrode plate from absorbing moisture, being damaged or the like, and the electrode performance from deterioration.

Further, the core, the cushioning, the flange and the core cap can be easily made of inexpensive material preferably with low impact on the environment at disposal. Hence, it is possible to reduce the total cost including the production cost and the distribution cost as collection of packaging material from transported location after the material is used once is not necessary but they can be discarded.

BRIEF DESCRIPTION OF THE DRAWINGS

In the accompanying drawings.

The sign in each figure refers to the following: 1 a roll of a long electrode plate; 2 a long electrode plate; 3 a core; 4 a cushioning; 5 a flange; 6 a core cap; 7 a cushioning; 8 a flange; 9 a core cap; 10 a cylindrical portion; 11 a collar portion; 12 a cylindrical portion; 13 a collar portion; 14 a core hole; 15 a cushioning hole; 16 a flange hole; 17 a cushioning hole; 18 a flange hole; 19 a pouch; 20 an adhesive portion; 21 a rib; 22 a rib; 23 a taper; 24 a rib.

DETAILED DESCRIPTION OF THE PREFERRED EMBODIMENT

Hereinafter, with reference to figures, the embodiment of the present invention will be explained in more detail.

Figure 5:
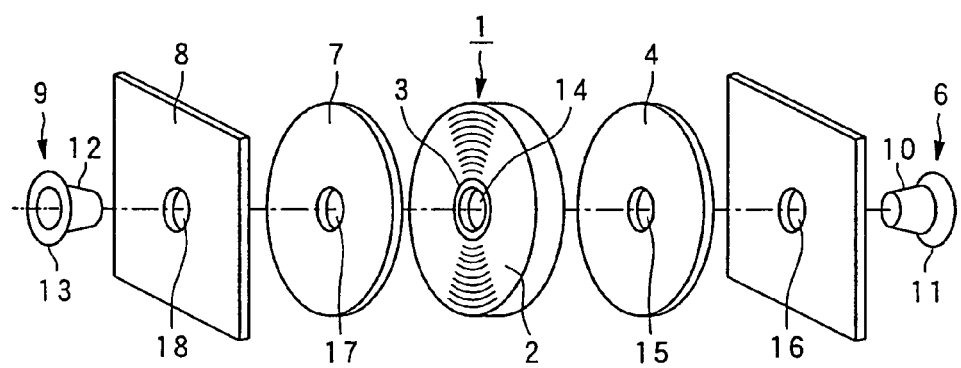
FIG. 5 is a perspective view showing a disassembled state of a package containing a roll of a long electrode plate of the present invention.

FIG. 5 is a perspective view showing a disassembled state of a package containing a roll of a long electrode plate of the present invention.

As members comprising the package containing a roll of a long electrode plate, there are a roll of a long electrode plate 1 wherein a long electrode plate 2 is wound to a core 3, a pair of cushionings 4 and 7, a pair of flanges 5 and 8, a pair of core caps 6 and 9. The flange 5 is arranged on the side surface of the roll of a long electrode plate 1 disposing the cushioning 4 therebetween so that axis of a hole 14 of the core 3, a hole 15 of the cushioning 4 and a hole 16 of the flange 5 align, and the roll of a long electrode plate 1, the cushioning 4 and the flange 5 are assembled by fitting a cylindrical portion 10 of the core cap 6 from the hole 16 of the flange 5 side, the core cap 6 comprising the cylindrical portion 10, which fits into each hole, and a collar portion 11. Also, the flange 8 is arranged on the other side surface of the roll of a long electrode plate 1 disposing the cushioning 7 therebetween so that axis of the hole 14 of the core 3, a hole 17 of the cushioning 7 and a hole 18 of the flange 8 align, and the roll of a long electrode plate 1, the cushioning 7 and the flange 8 are assembled by fitting a cylindrical portion 12 of the core cap 9 from the hole 18 of the flange 8 side, the core cap 9 comprising the cylindrical portion 12, which fits into each hole, and a collar portion 13. Thus, the cushioning and the flange are assembled on both side surfaces of the roll of a long electrode plate 1.

Figure 6:
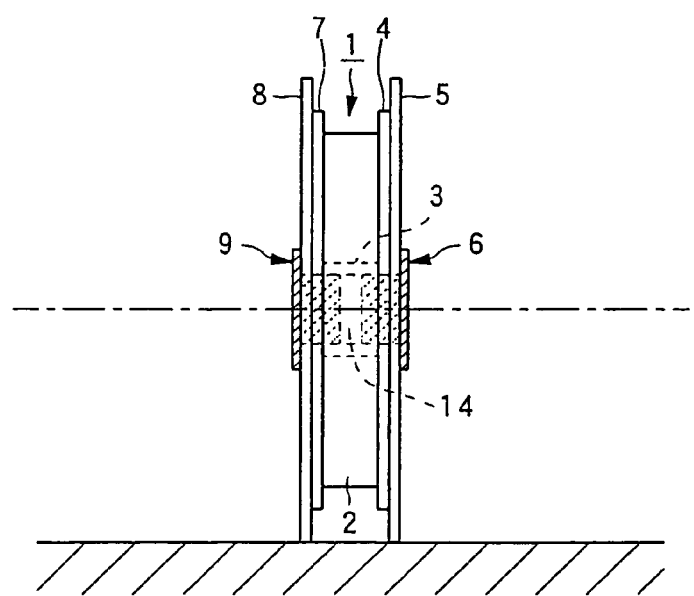
FIG. 6 is a side view showing an assembled state of a package containing a roll of a long electrode plate of the present invention.

Further, FIG. 6 is a side view showing an assembled state of a package containing a roll of a long electrode plate of the present invention. FIG. 6 shows an assembled state of each member comprising the package containing a roll of a long electrode plate as shown in FIG. 5. The core cap 6 is used to mount the flange 5 on the side surface of the roll of a long electrode plate 1 disposing the cushioning 4 therebetween. The cylindrical portion 10 of the core cap 6 is fitted into holes 14, 15 and 16 so that the hole 16 of the flange 5, the hole 15 of the cushioning 4 and the hole 14 of the core 3 align. Similarly, the core cap 9 is used to mount the flange 8 on the other side surface of the roll of a long electrode plate 1 disposing the cushioning 7 therebetween, and the cylindrical portion 12 of the core cap 9 is fitted into holes 14, 17 and 18 so that the hole 18 of the flange 8, the hole 17 of the cushioning 7 and the hole 14 of the core 3 align. A taper form or a partial protruding form may be applied to an outer circumferential surface of a cylindrical portion of the core cap. Thereby, it is possible to increase adhesion of fitting between the core caps 6 and 9 and each hole so that the members will not come off easily once they are mounted.

Further, as shown in FIG. 6, when flanges 5 and 8 are arranged to align on the same axis on both side surfaces of the roll of a long plate 1, each configuration of the pair of flanges 5 and 8 is larger than that of the roll of a long electrode plate 1, thus the pair of flanges 5 and 8 is grounded to suspend and support the roll of a long electrode plate 1. Also, it is preferable to enlarge the configuration of the pair of cushionings 4 and 7 with respect to the configuration of the roll of a long electrode plate 1, in order to protect the roll of a long electrode plate from contacting the flanges 5 and 8. Further, with regard to the relationship of size between the pair of flanges and the pair of cushionings when the pair of flanges, the pair of cushionings and the roll of a long plate 1 are arranged on same axis, configurations of both pair of flanges and pair of cushionings are larger than that of the roll of a long electrode plate. Furthermore, it is preferable that configuration of the flange is larger than that of the cushioning, or both flange and cushioning are in the same size since workability improves at the time of packaging with a pouch or the like. It is further preferable that the flange, the cushioning and the core cap used in the present invention are respectively used in a pair wherein the pair is in the same size and made of the same material. It is because at the time of aligning and assembling each member to comprise a package, members can be used in free combination without distinguishing right-and-left, or number of kinds of members used can be less so that supplying cost of material can be reduced.

Figure 7:
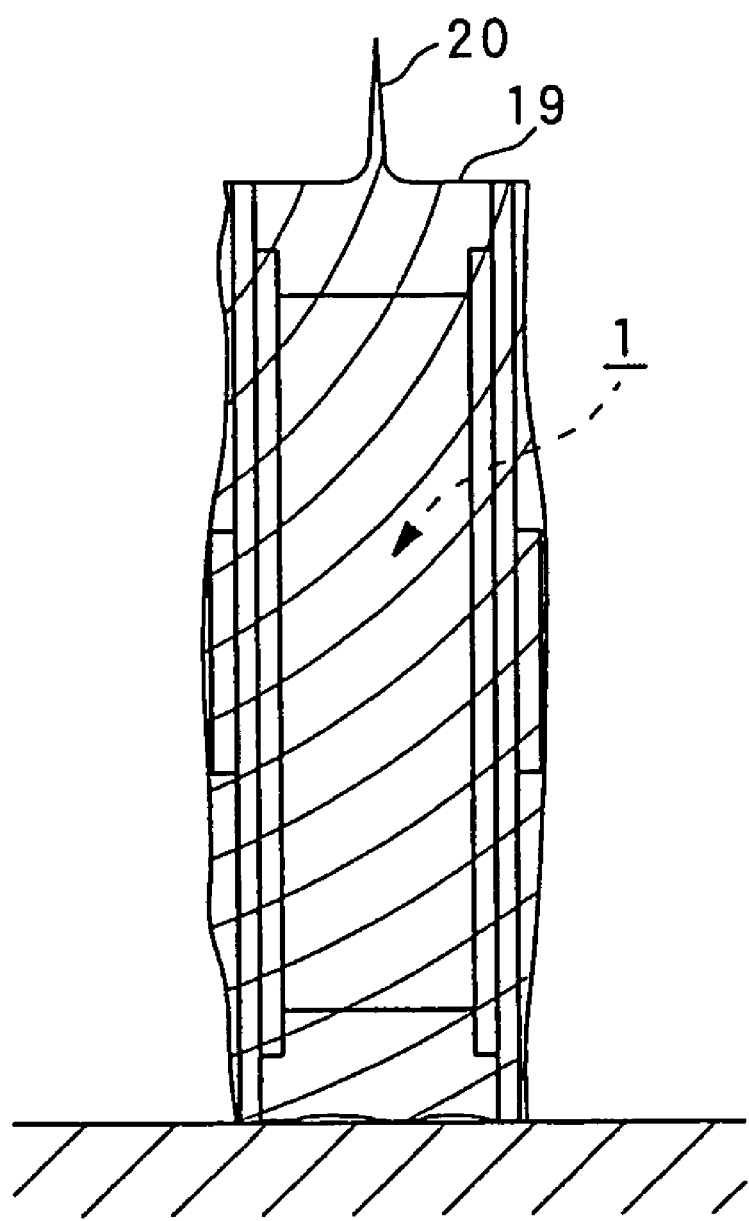
FIG. 7 is a side view showing a packaged state of a package containing a roll of a long electrode plate of the present invention in a pouch.

FIG. 7 is a side view showing a packaged state of a package containing a roll of a long electrode plat of the present invention in a pouch. The flange is mounted on both side surfaces of the roll of a long electrode plate disposing the cushioning therebetween by letting the cylindrical portion of the core cap into holes in the center of each member so that it is in the state that the roll of a long electrode plate is not grounded but the pair of flanges is grounded to suspend and support the roll of a long electrode plate, and packed in a pouch 19 to cover entirely. For example, depressurized dry air is fed to the pouch 19 in which the roll of a long electrode plate and other members are contained. Then, an opening of the pouch is adhered and sealed by heat sealing. In FIG. 7, the sign 20 refers to an adhesive portion of heat sealing.

Hereinafter, each member comprising the package containing a roll of a long electrode plate will be explained in more detail.

(Electrode Plate)

The electrode plate of the present invention is applied to an electrode plate for lithium-ion battery, an electrode plate for an electric double layer capacitor, an electrode plate for fuel cell or the like. In any cases, it is in a form that a long electrode plate is wound to a core. Hereinafter, an electrode for lithium-ion battery will be explained in more detail, however, the present invention is not limited thereto. In the case of an electric double layer capacitor, the capacitor has a laminated structure of plural electrode plates wherein active material layers are provided on a collector. The present invention can be applied to the electrode plate. Further, in the case of a fuel cell, a fuel cell comprises an electrode plate wherein an electrocatalyst layer containing catalyst, electrode active material or the like necessary for electrode reaction is provided on a collector. The present invention can be applied to the electrode plate. In this manner, an electrode plate may not be limited if it comprises a long (consecutive) collector (an electrode substrate) on which an active material layer is provided and wound continuously to a core.

The electrode plate has formed an active material layer (positive) which emits ions or an active material layer (negative) which absorbs the ions on a collector, and has a portion which does not have active material layer provided in pattern form as a terminal fixing portion.

As the collector which is a substrate, generally a metal foil is used. As a positive electrode plate, an aluminum foil is preferably used. As a negative electrode plate, a copper foil is preferably used. The thickness of these metal foils is generally about 10 to 50 µm.

Prior to formation of an active material layer by applying an active material coating liquid containing at least an active material and a binder on one side or both sides of a collector and drying the coated layer, a coupling agent layer may be formed on a surface of the collector in order to improve adhesion between the collector and the active material layer. As a coupling agent, for example, a coupling agent such as silanes, titanates, aluminums or the like can be used. Among them, a coupling agent having good adhesion between the collector made of metal foil and the active material layer is selected for use.

As the active material, there are positive active material and negative active material. As the positive active material, for example, there may be lithium oxide such as $LiCoO_2$, $LiNiO_2$, $LiMn_2O_4$ or the like, or chalcogen compound such as $TiS_2$, $MnO_2$, $MoO_3$, $V_2O_5$ or the like. The positive active material may be used solely or in combination of two or more kinds. As the negative active material, for example, lithium containing metal such as metal lithium or lithium alloy, graphite, carbon black, or carbonaceous material such as acetylene black may be used. Particularly, if $LiCoO_2$ or $LiMn_2O_4$ is used as a positive active material and carbonaceous material is used as negative active material, a lithium secondary battery having high discharge voltage of about 4 volt can be obtained. It is preferable that the positive active material and the negative active material have particle size of about 1 to 100 µm to disperse the active material in an active material layer evenly, and are in powder form having a mean particle size of 5 to 40 µm.

It is necessary that the binder is electrochemically stable with respect to a nonaqueous electrolyte, does not elute into electrolyte, and is soluble to a solvent so that a coating liquid can be thinly applied on a collector made of a metal foil. As the binder, for example, thermoplastic resin, more specifically, polyester resin, polyamide resin, polyacrylic acid ester resin, polycarbonate resin, polyurethane resin, cellulose resin, polyolefin resin, polyvinyl resin, fluorine based resin, polyimide resin or the like may be used. An acrylate monomer or oligomer having a reactive functional group introduced may be mixed in the binder. Besides the above, heat-curable resins such as rubber based resin, acrylic resin, urethane resin or the like, acrylate monomer, acrylate oligomer or ionizing radiation-curable resin comprising the mixture thereof, and a mixture of the above resins may be used.

The coating liquid is prepared in such manner that accordingly selected active material and binder are provided in a dispersant or a solvent comprising an organic solvent such as N-methyl-2-pyrrolidone, toluene, methylethyl ketone or a mixture thereof or water, a conductive material is mixed therein as required, and the mixture is mixed and dispersed in a disperser such as a homogenizer, a ball mill, a sand mill, a roll mill, a planetary mixer or the like. With respect to the whole coating liquid as 100 parts by weight, a total amount of the active material and the binder is preferably about 40 to 90 parts by weight. Also, compound ratio of the active material and the binder may be as same as a conventional method. For example, in the case of a positive active material, approximately "binder:active material=0.5:0.5 to 0.01:0.99 (in mass ratio)" is preferable, and in the case of a negative active material, approximately "binder:active material=0.5:0.5 to 0.01:0.99 (in mass ratio) is preferable. As the conductive material, for example, graphite, carbon black, carbonaceous material such as acetylene black or the like may be used as required.

The prepared coating liquid is applied on a collector which is a substrate by a method such as gravure coating, gravure reverse coating, roll coating, Mayor bar coating, blade coating, knife coating, air knife coating, slot die coating, slide die coating, dip coating, die coating, comma roll coating, comma reverse coating or the like, and dried to form an active material layer.

(Core)

As the core 3, which winds the roll of a long electrode plate, a core made of metal such as aluminum or the like, a molding worked in a molding resin such as polyethylene, polypropylene or the like in view of toughness and the lightness in weight, a paper tube which generates less paper powder or the like and has the containing amount of water controlled to be small or the like may be used. However, since a member of a package containing a roll of a long electrode plate of the present invention is to be thrown away after use, a general synthesized resin or a paper tube is preferable.

(Cushioning)

As the cushioning 4, generally, sponge, foamed urethane, glass wool, foamed rubber or the like may be used. The cushioning protects the roll of a long electrode plate and the flange from direct contact thereof and side surfaces of the roll of a long electrode plate from damage by friction, impact or the like. Also, it is preferable to select material among the above that does not drop off powder or the like from the cushioning when handling the cushioning itself or when the cushioning is packed together in a roll of a long electrode plate. The attachment of foreign substance such as powder of the like to the electrode plate leads to deterioration of performance of the electrode plate.

The size of the cushioning may be preferably same among a pair, and may be same as the size of configuration of side surface of the roll of a long electrode plate 1 or larger than that so that the cushioning covers whole side surface of the roll of a long electrode plate when the cushioning is arranged on the side surface of the roll of a long electrode plate to align on same axis. Also, the configuration of the cushioning may not be limited to a round as shown in FIG. 5, but it may be of any configurations such as tetragon or the like if it covers whole side surface of roll of the long electrode plate.

(Flange)

As the flange 5, a molding worked in a molding resin such as polyethylene, polypropylene or the like in view of toughness and the lightness in weight may be used. Particularly, it is preferable to use light and highly rigid material made of polypropylene resin such as SUNPLY (product name; manufactured by Sumika Plastech Co., Ltd.), which has a structure disposing plural ribs between a pair of thin plates made of thermoplastic resin arranged in parallel. In this manner, it is preferable that the resin itself has toughness, and provides space (void) disposing a rib therebetween, and further the thermoplastic resin used is expanded, thereby, the weight of the flange can be lighter.

The size of the flange may be preferably same among a pair, and both configurations of the pair of flanges are made larger than that of the side surface of the roll of a long electrode plate when the flange is arranged on the side surface of the roll of a long electrode plate on same axis so that a whole side surface of the roll of a long electrode plate is covered disposing the cushioning therebetween, and the roll of a long electrode plate is not grounded. Thereby, the pair of flanges is grounded to suspend and support the roll of a long electrode plate. The configuration of the flange may not be limited to a tetragon as shown in FIG. 5, but it may be of any configurations such as rectangle, trapezium or the like if it exhibits the above function.

(Core Cap)

As the core cap 6, a molding worked in a molding resin such as polyethylene, polypropylene or the like in view of toughness and the lightness in weight may be used.

Figure 8:
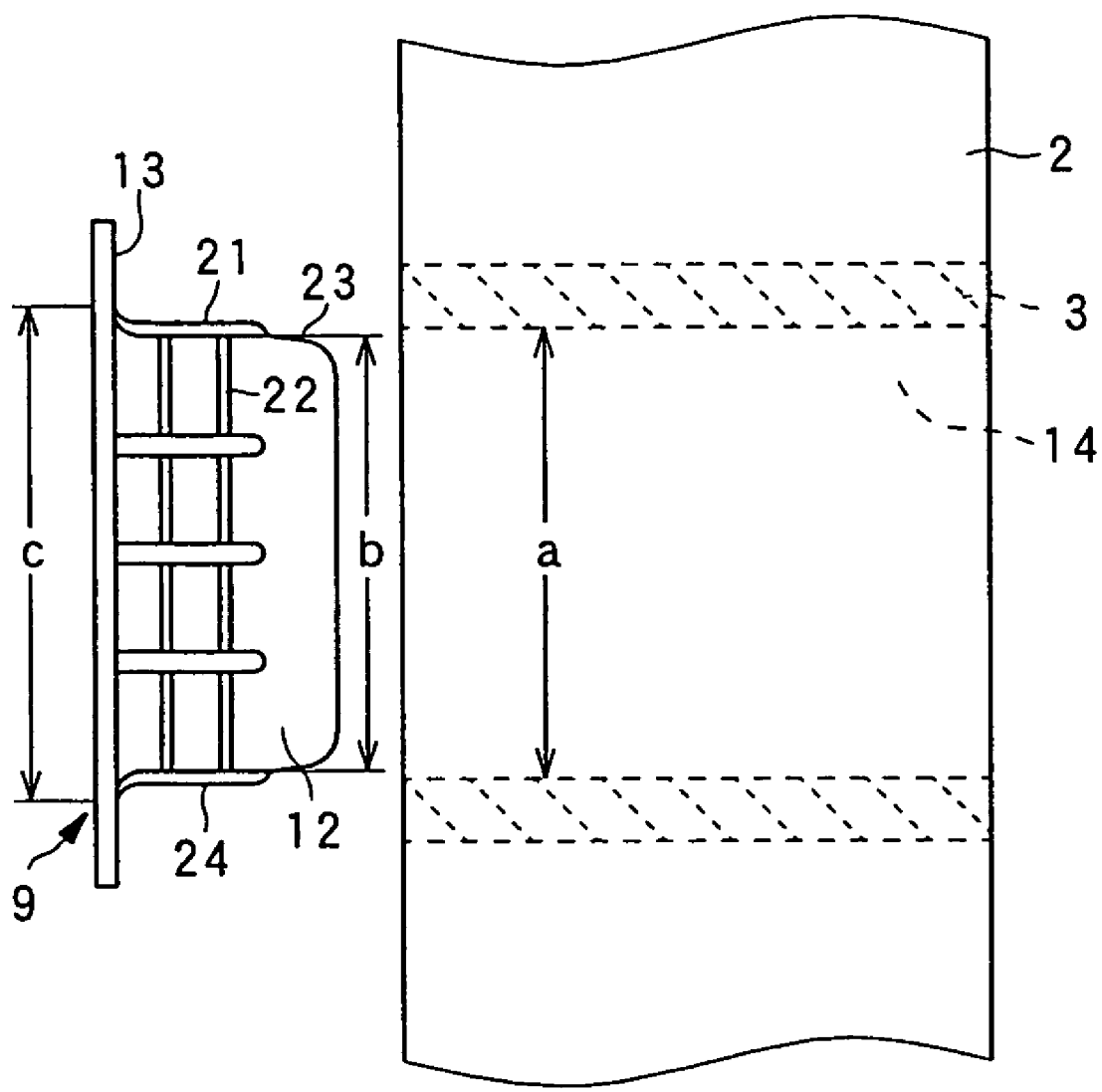
FIG. 8 is a schematic view schematically showing a core cap fitting to a core hole which has wound a long electrode plate.

The core cap mainly comprises the cylindrical portion and the collar portion. It is preferable to increase adhesion in fitting between the core cap and each hole of the flange, the cushioning and the core by applying a taper form or a partial protruding form to an outer circumferential surface of the cylindrical portion. For example, FIG. 8 is a schematic view schematically showing the core cap 9 fitting to the hole 14 of the core 3 which has wound the long electrode plate 2. Hereinafter, the present invention will be explained in refer to FIG. 8. In order to simplify the explanation and avoid complex drawing, the cushioning and the flange, which are actually disposed between the core cap and the roll of a long electrode plate, are abbreviated in the drawing.

In FIG. 8, ribs 21 are formed on the outer circumferential surface of the cylindrical portion 12 of the core cap 9 at even intervals in parallel with a center axis of the core cap 9. Also, two ring-form ribs 22 are formed surrounding the outer circumferential surface of the cylindrical portion 12. In order to facilitate insertion of the core cap 9, it is preferable that an end of the rib 21 will not reach an end portion of the core cap 9 and the ring-form rib 22 is not formed at an end portion of the cylindrical portion.

Comparing the diameter "a" of the hole 14 of the core 3 with the diameter "b" of the end portion of the cylindrical portion 12 of the core cap 9, it is preferable that there is a relationship of a>b, the diameter "a" of the hole of the core 3 and the distance (outside diameter) between the rib 21 and the rib 24, which are in opposite position on circumference of the cylindrical portion, are of the same length or the diameter "a" is larger in size about 0.05 mm to 0.1 mm. Thereby, it is easier to mount the cylindrical portion 12 to the core 3 and adhesion therebetween is good.

If the location where the cylindrical portion 12 and the collar portion 13 of the core cap 9 contact are made to have a taper form, and the diameter "c" of the base of the cylindrical portion 12 is made larger than the diameter "a" of the hole 14 of the core 3 in about 0.05 to 0.5 mm, the core cap 9 and the core 3 fit firmly so that the members will not come off easily once they are fitted.

In this manner, by making the location from the end of the cylindrical portion 12 of the core cap 9 to the end portion of the rib 21 have the taper 23 form, it becomes easier to insert the cylindrical portion 12 in the hole 14 of the core 3, thus it is preferable.

Further, the end portion of the rib 21 may be made to have the taper form which lowers to the end in order to decrease resistance slightly upon insertion of the rib 21 to the hole 14 of the core 3. The rib 21 may be formed in height of about 0.05 mm to 1 mm.

Also, the ring-form rib 22 can function as a stopper to prevent the core cap 9 from coming off easily from the hole 14 of the core 3 after the core cap 9 is mounted on the hole 14 of the core 3 during handling, transport or the like. It is desirable to lower the height of the ring-form rib 22 than that of the rib 21 in order to improve workability at the time of fitting the core cap 9 to the hole 14 of the core 3.

(Pouch)

In the package containing a roll of a long electrode plate of the present invention, the roll of a long electrode plate is packed together with at least gas.

The material used for the package is not limited if it is airtight and can maintain dry condition of inside the package. A pouch may be made of inexpensive material with low impact on the environment at disposal, thus it is suitable to be thrown away after use.

As the pouch, it is desirable to use a bag having one side open in a certain size and the other three sides sealed in advance upon use. The pouch is not limited to a three side seal type, but a pillow type, a gusset type, a tetra-pack type, a stand pouch type or the like may be adopted.

The pouch 19 may preferably comprise a laminated material wherein a layer having deposited metal such as aluminum or the like or a metal foil is laminated on a substrate, and further a resin layer having heat sealing characteristics is provide thereon. Thereby, the pouch with excellent gas barrier properties against air charged with moisture or the like can be obtained.

As the substrate comprising the laminated material of the pouch, for example, a resin film or sheet having excellent mechanical, physical and chemical characteristics or the like may be used, particularly, a resin film or sheet having excellent strength, toughness and heat resistance may be used. Specifically, there may be a tough oriented (uniaxial or biaxial) or unoriented film or sheet made of resin such as polyester based resin, polyamide based resin, polyaramid based resin, polyolefin based resin, polycarbonate based resin, polystyrene based resin, polyacetal based resin, fluorine based resin or the like. The thickness of the substrate may be about 5 to 100 μm, preferably about 10 to 50 μm.

Also, the metal foil or the metal deposition layer comprising the laminated material may have the substrate laminated with metal foil made of aluminum, iron, copper, nickel or the like or form the deposition layer on the substrate using metal such as aluminum, titanium, silicon or the like or metal oxides thereof. The thickness of the metal foil or the metal deposition layer may be about 0.05 μm to 15 μm.

As for the laminated material of the pouch, the resin layer having heat sealing characteristics may be provided on the metal foil or the metal deposition layer formed on the substrate. As for resin having heat sealing characteristics used for the resin layer having heat sealing characteristics, there may be mutually fusible resin which melts by heat. Specifically, acid-modified polyolefin resin, polyvinyl acetate based resin, poly(meth)acrylic based resin, polyvinyl chloride based resin or the like wherein polyolefin based resin such as low density polyethylene, medium density polyethylene, high density polyethylene, straight-chain (linear) low density polyethylene, polypropylene, ethylene vinyl acetate copolymer, ionomer resin, ethylene-acrylic acid copolymer, ethylene-methacrylic acid copolymer, ethylene-methacrylic methyl copolymer, ethylene-propylene copolymer, methylpentene polymer, polybutene polymer, polyethylene, polypropylene or the like is modified by unsaturated carboxylic acid such as acrylic acid, methacrylic acid, maleic acid, maleic anhydride, fumaric acid, itaconic acid or the like may be used. The resin layer having heat sealing characteristics may be formed by applying the above mentioned resin having heat sealing characteristics or by laminating the film or sheet made of the resin having heat sealing characteristics. The thickness of the resin layer having heat sealing characteristics may be in the range of 5 to 300 μm, preferably 10 to 100 μm.

The thickness of the pouch comprising the above mentioned laminated material may be about 20 to 500 μm.

An assemblage including the roll of a long electrode plate and other members is contained in the pouch. For example, dry air or inert gas such as nitrogen or the like may be fed into the pouch under reduced pressure, a gas replacement is performed by the fed gas inside of the pouch, an opening of the pouch is heated, adhered and sealed superposing resin layers having heat sealing characteristics to face each other. Since the pouch contained the roll of a long electrode plate is filled with dry gas which has no moisture or negligible amount of moisture and sealed, thus, moisture absorption or other change in characteristics with time of the roll of a long electrode plate can be prevented.

The gas replacement in the pouch is not based on the premise that it is performed under reduced pressure. It is possible to fill the pouch with the gas for the replacement under normal atmospheric pressure and exhaust air which originally existed in the pouch. If the gas replacement is performed under reduced pressure or under vacuum, the replacement rate of the gas replacement increases and change in characteristics with time by moisture absorption or the like can be prevented in high accuracy.

As other embodiment besides the above mentioned gas flush packaging, a desiccating agent such as quicklime, silica gel or the like having moisture absorption property may be added and stored in the pouch, or both gas flush packaging and method using the desiccating agent may be used together. The combination method is preferable as it is possible to reduce moisture in the pouch even further.

As mentioned above, it is possible to fill the pouch containing the roll of a long electrode plate with gas and transport the pouch as it is. However, it is preferable to set one or more pouches containing the roll of a long electrode plate in a fiberboard container, and further to tape the fiberboard container so that the quality of the roll of a long electrode plate will not deteriorate by vibration or impact during transport or the like.

Even if an external packaging such as the fiberboard container or the like is performed to the package containing a roll of a long electrode plate of the present invention, it is important that the condition that the roll of a long electrode plate is not grounded and suspended in midair during the storage and transportation is constantly maintained. Thereby, the roll will not be damaged or the like and the deterioration of the electrode performance can be prevented.

Further, as thus far described, the package comprises a roll of a long electrode plate comprising a long electrode plate wound to a core, a pair of cushionings, a pair of flanges and a pair of core caps. However, it is possible, for example, that side surfaces of two or more rolls of a long electrode plate may be located next to each other respectively disposing a cushioning therebetween, and plural rolls of a long electrode plate are supported and suspended by using a pair of flanges and a pair of core caps on both ends. It is, however, necessary to lengthen the cylindrical portion of the core cap to be able to support plural rolls of the long electrode plate. Then, including pairs of flanges on the ends, plural rolls of a long electrode plate can be contained in one pouch.

EXAMPLE 1

Next, the following examples and comparative examples further describe the present invention.

A package containing a roll of a long electrode plate as shown in FIGS. 5 and 6 was prepared as follows.

(Preparation of a Long Electrode Plate)

As material of an electrode plate coating liquid, 85 parts by weight of activated carbon powder, 7 parts by weight of conductive material, 5 parts by weight of SBR (styrene-butadiene rubber) resin, 3 parts by weight of CMC (carboxymethyl cellulose) and 300 parts by weight of water as dispersing medium were used in the compound ratio and mixed in a planetary mixer (manufactured by KODAIRA SEISAKUSHO CO., LTD.) for 30 minutes to obtain a coating liquid containing active material as slurry.

Figure 3A:
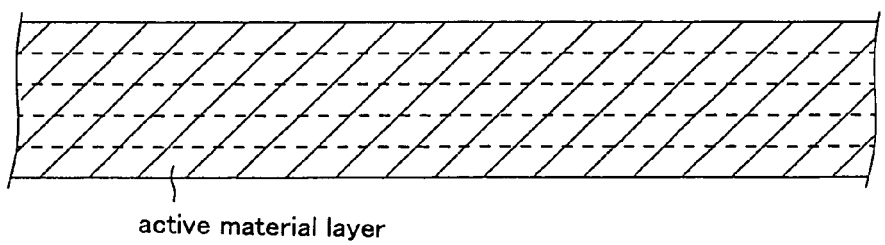
FIG. 3 is a schematic view schematically showing an electrode plate.
Figure 3B:
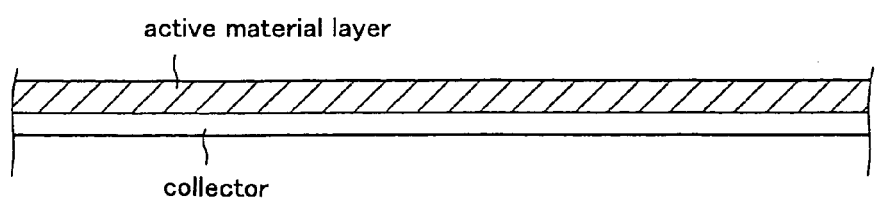
Figure 4:
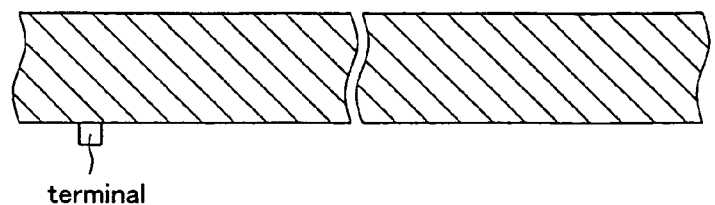
FIG. 4 is a schematic view schematically showing an electrode plate cut in long plate form.

Using the obtained coating liquid, the coating liquid was applied on a collector made of etching aluminum foil having thickness of 20 μm and width of 300 mm by die coater as shown in FIG. 3. Then, the coated collector was dried at 140° C. for 10 minutes to form a coating layer on the etching aluminum foil, and slit up by a slitter. Thus obtained coating layer containing active material was subject to aging at 80° C. in a vacuum oven for 48 hours to remove moisture, thereby, an electrode plate for capacitor was prepared. The electrode plate was a long continuous plate having width of 56 mm and wound to a core made of polypropylene.

As a cushioning, a pair of rounds (with a hole in each center) made of foamed urethane having thickness of 3 mm as shown in FIG. 5 was prepared. As a flange, a pair of sheets was prepared by cutting a sheet having a hollow structure made of polypropylene resin of HP50120 (product name: SUNPLY, manufactured by Sumika Plastech Co., Ltd.) in square as shown in FIG. 5 and forming a hole in the center. Further, a pair of core caps was prepared by injection molding of polypropylene resin in a form as shown in FIG. 5.

The flange was mounted on both sides of the thus obtained roll of a long electrode plate wherein the long electrode plate was wound to the core disposing the cushioning therebetween so as to align the core hole, the cushioning hole and the flange hole. A cylindrical portion of the core cap comprising the cylindrical portion, which fits in each hole, and a collar portion was fitted from a hole on the side of the flange. Further, the whole thing including the pair of cushionings, flanges and core caps and the roll of a long electrode plate was packed in a pouch, which is a three side seal type made of a laminated material comprised of polypropylene resin layer (50 μm)/aluminum layer (5 μm)/polyethylene resin layer (50 μm), and dry air was sufficiently fed in the pouch under decreased pressure. By the thus fed gas, a gas replacement was performed inside of the pouch. An opening of the pouch was heated to adhere contacting polypropylene resin layers, which are resin layers having heat sealing characteristics, each other, and the pouch was sealed. Thus, it was in the state that the pair of flanges is grounded to suspend and support the roll of a long electrode plate.

5 units of the package containing a roll of a long electrode plate were prepared in the same condition as above. The 5 units were placed to locate flanges next to each other and contained in a fiberboard container. Finally, outside of the fiberboard container was taped by a tape made of vinyl chloride. The roll of a long electrode plate was stored and transported so that the condition that the roll of a long electrode plate contained in the fiberboard container was not grounded and suspended in midair was constantly maintained.

At the transported location, the package was opened to observe the roll of a long electrode plate. There was no damage or weaving. Also, deterioration of the electrode performance was not observed. Further, after using the long electrode plate, it was not necessary to collect the packaging material mainly comprising the core, the cushioning, the flange and the core cap and able to discard the material at the transported location.

EXAMPLE 2

(Preparation of a Positive Long Electrode Plate)

As material of a positive coating liquid, 90 parts by weight of $LiCoO_2$ powder having particle size of 1 to 100 μm and a mean particle size of 10 μm, 5.0 parts by weight of graphite powder as conductive material, 5 parts by weight of polyvinyliden fluoride resin (product name: NEOFLON VDF, VP-850, manufactured by DAIKIN INDUSTRIES, CO. LTD.) as binder and 50 parts by weight of N-methylpyrrolidone were used in the compound ratio. Among these materials, polyvinyliden fluoride was solved by N-methylpyrrolidone to prepare a varnish. After other powder material was added to the obtained varnish, it was agitated to mix by a planetary mixer (manufactured by KODAIRA SEISAKUSHO CO., LTD.) for 30 minutes to obtain a positive coating liquid containing positive active material as slurry.

Figure 1A:
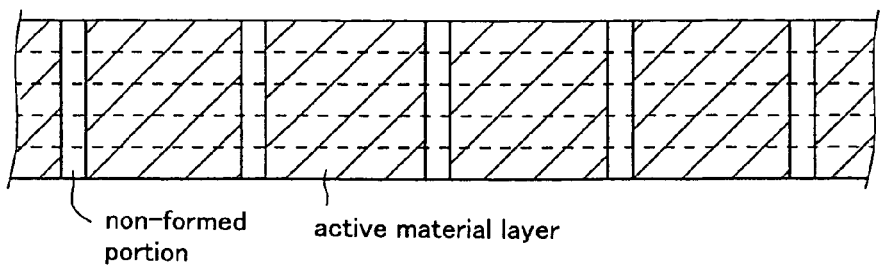
FIG. 1 is a schematic view schematically showing an electrode plate.
Figure 1B:
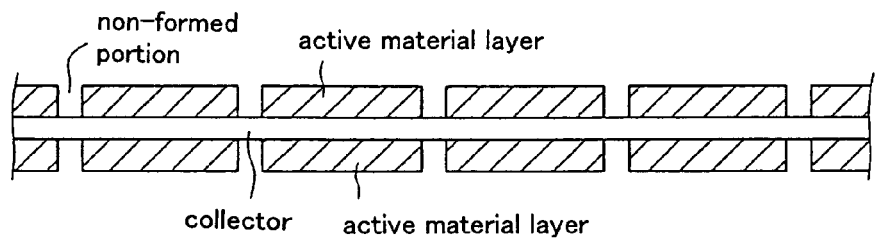
Figure 2:
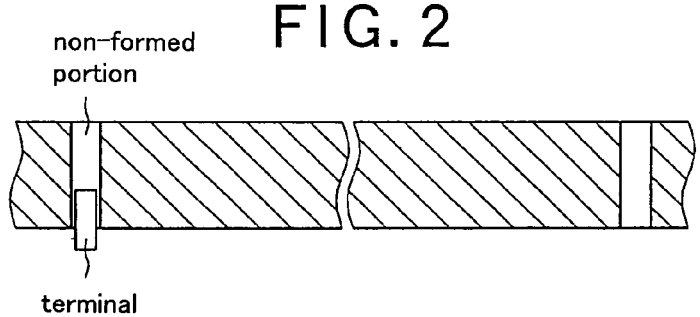
FIG. 2 is a schematic view schematically showing an electrode plate cut in long plate form.

Using thus obtained positive coating liquid, the positive active material coating liquid was applied on a collector made of aluminum foil having thickness of 15 μm and width of 300 mm by die coater to form a pattern as shown in FIG. 1. Then, the coated collector was dried at 140° C. for 10 minutes to form a coating layer on the aluminum foil, further pressed at line pressure of 1 t/cm by a roll press machine and slit up by a slitter. Further, thus obtained coating layer containing positive active material was subject to aging at 80° C. in a vacuum oven for 48 hours to remove moisture and a positive electrode plate was prepared. The electrode plate was a long continuous plate having width of 56 mm and wound to a core made of polypropylene.

As a cushioning, a pair of rounds (with a hole in each center) made of foamed urethane having thickness of 3 mm as shown in FIG. 5 was prepared. As a flange, a pair of sheets was prepared by cutting a sheet having a hollow structure made of polypropylene resin of HP50120 (product name: SUNPLY, manufactured by Sumika Plastech Co., Ltd.) in square as shown in FIG. 5 and forming a hole in the center. Further, a pair of core caps was prepared by injection molding of polypropylene resin in a form as shown in FIG. 5.

The flange was mounted on both sides of the thus obtained roll of a long electrode plate wherein the long electrode plate was wound to the core disposing the cushioning therebetween so as to align the core hole, the cushioning hole, the flange hole. A cylindrical portion of the core cap comprising the cylindrical portion, which fits each hole, and a collar portion was fitted from a hole on the side of the flange. Further, the whole thing including the pair of cushionings, flanges and core caps and the roll of a long electrode plate was packed in a pouch, which is a three side seal type made of a laminated material comprised of polypropylene resin layer (50 μm)/aluminum layer (5 μm)/polyethylene resin layer (50 μm), and dry air was sufficiently fed in the pouch under decreased pressure. By the thus fed gas, a gas replacement was performed inside of the pouch. An opening of the pouch was heated to adhere contacting polypropylene resin layers, which are resin layers having heat sealing characteristics, each other, and the pouch was sealed. Thus, it was in the state that the pair of flanges was grounded to suspend and support the roll of a long electrode plate.

5 units of the package containing a roll of a long electrode plate were prepared in the same condition as above. The 5 units were placed to locate flanges next to each other and contained in a fiberboard container. Finally, outside of the fiberboard container was taped by a tape made of vinyl chloride. The roll of a long electrode plate was store and transported so that the condition that the roll of a long electrode plate contained in the fiberboard container was not grounded and suspended in midair was constantly maintained.

At the transported location, the package was opened to observe the roll of a long electrode plate. There was no damage or weaving. Also, deterioration of the electrode performance was not observed. Further, after using the long electrode plate, it was not necessary to collect the packaging material mainly comprising the core, the cushioning, the flange and the core cap and able to discard the material at the transported location.

EXAMPLE 3

A package containing a roll of a long electrode plate as shown in FIGS. 5 and 6 was prepared as follows.

(Preparation of a Negative Long Electrode Plate)

As material of a negative coating liquid, 90 parts by weight of graphite powder, 10 parts by weight of polyvinyliden fluoride resin (product name: NEOFLON VDF, VP-850, manufactured by DAIKIN INDUSTRIES, CO. LTD.) and 80 parts by weight of N-methylpyrrolidone as dispersing medium were used in the compound ratio. The powders were dispersed using the same disperser and dispersing method as preparing the positive coating liquid to obtain a negative coating liquid as slurry.

Using thus obtained negative coating liquid, the negative coating liquid was coated on a collector made of pressed copper foil having thickness of 12 μm and width of 300 mm by die coater to form a pattern as shown in FIG. 1. Then, the coated collector was dried at 140° C. for 10 minutes to form a coating layer on the copper foil, further pressed at line pressure of 0.5 t/m by a roll press machine and slit up by a slitter. Further, as in the same manner as forming the positive electrode plate, moisture was removed to prepare a negative electrode plate. The electrode plate was a long continuous plate having width of 57.5 mm and wound to a core made of polypropylene.

The roll of a long electrode plate and a pair of cushionings, flanges and core caps of the same condition as Example 2 were prepared, packed in the similar pouch used in Example 2, subjected to similar gas replacement, and sealed to prepare a package. Thus, it was in the state that the pair of flanges was grounded to suspend and support the roll of a long electrode plate.

5 units of the package containing a roll of a long electrode plate were prepared in the same condition as above. Similarly as in Example 2, the 5 units were placed to locate flanges next to each other and contained in a fiberboard container. Finally, outside of the fiberboard container was taped by a tape made of vinyl chloride. The roll of a long electrode plate was stored and transported so that the condition that the roll of a long electrode plate contained in the fiberboard container was not grounded and suspended in midair was constantly maintained.

At the transported location, the package was opened to observe the roll of a long electrode plate. There was no damage or weaving. Also, deterioration of the electrode performance was not observed. Further, after using the long electrode plate, it was not necessary to collect the packaging material mainly comprising the core, the cushioning, the flange and the core cap and able to discard the material at the transported location.

What is claimed is:

1. A package containing a roll of a long electrode plate, wherein a pair of sheet cushionings having a hole and a pair of sheet flanges having a hole are respectively arranged in this order on both side surfaces of a roll of a long electrode plate comprising a core having a hole and a long electrode plate, which is wound to the core, or on both side surfaces of a group of rolls of a long electrode plate comprising two or more rolls of a long electrode plate and one or more cushionings disposed alternatively so that the side surfaces of the rolls of a long electrode plate are located next to each other disposing the cushioning having a hole therebetween, so as to align the core hole, the cushioning hole and the flange hole;

wherein an assemblage in which the roll of a long electrode plate, the cushionings, the flanges and a pair of core caps are assembled by fitting a cylindrical portion of the core caps from the flange hole side is contained in a 20 to 500 μm thick pouch with dry gas or a desiccating agent, the core cap comprising the cylindrical portion, which fits into each hole, and a collar portion;

wherein the pair of flanges are grounded to suspend and support the roll of a long electrode plate by making both configurations of the pair of flanges larger than that of the roll of a long electrode plate in order to prevent the roll of a long electrode plate from being grounded;

wherein a taper form or a partial protruding form is applied to an outer circumferential surface of the cylindrical portion of the core cap; and wherein the flange has a structure disposing plural ribs between a pair of thin plates made of thermoplastic resin, wherein ribs are formed on the outer circumferential surface of the cylindrical portion of the core cap in parallel with a center axis of the core cap, whch are about 0.05 mm to 1 mm in height, and ring-form ribs are formed surrounding the outer circumferential surface of the cylindrical portion, which are lower in the height than the parallel ribs.

2. The package containing a roll of a long electrode plate according to claim 1, wherein a taper form is applied to an outer circumferential surface of the cylindrical portion of the core cap;

a diameter of an end portion of the cylindrical portion is smaller than a diameter of the hole of the core; and a diameter of a base of the cylindrical portion is larger than the diameter of the hole of the core by about 0.05 to 0.5 mm.

3. The package containing a roll of a long electrode plate according to claim 1, wherein ribs are formed on the outer circumferential surface of the cylindrical portion of the core cap at even intervals in parallel with a center axis of the core cap, and the rib does not reach the end portion of the cylindrical portion.

4. The package containing a roll of a long electrode plate according to claim 1, wherein the core cap comprises a molding resin.

* * * * *